United States Patent
Ushiroda

(10) Patent No.: US 9,560,983 B2
(45) Date of Patent: Feb. 7, 2017

(54) METHOD FOR CREATING AND ANALYZING GRAPHS OF CARDIAC FUNCTION IN ATRIAL FIBRILLATION AND SINUS ARRHYTHMIA BASED ON THORACIC IMPEDANCE MEASUREMENTS

(71) Applicant: MEDICAL CORPORATION USHIRODA INTERNAL MEDICINE CLINIC, Iwaki-shi, Fukushima (JP)

(72) Inventor: Shinichi Ushiroda, Iwaki (JP)

(73) Assignee: MEDICAL CORPORATION USHIRODA INTERNAL MEDICINE CLINIC, Iwaki-Shi (JP)

( * ) Notice: Subject to any disclaimer, the term of this patent is extended or adjusted under 35 U.S.C. 154(b) by 0 days.

(21) Appl. No.: 14/758,013

(22) PCT Filed: Dec. 27, 2012

(86) PCT No.: PCT/JP2012/083864
§ 371 (c)(1),
(2) Date: Jun. 26, 2015

(87) PCT Pub. No.: WO2014/102964
PCT Pub. Date: Jul. 3, 2014

(65) Prior Publication Data
US 2015/0327790 A1 Nov. 19, 2015

(51) Int. Cl.
*A61B 5/0452* (2006.01)
*A61B 5/0245* (2006.01)
(Continued)

(52) U.S. Cl.
CPC ......... *A61B 5/04525* (2013.01); *A61B 5/0245* (2013.01); *A61B 5/044* (2013.01);
(Continued)

(58) Field of Classification Search
CPC ... A61B 5/0402; A61B 5/0537; A61B 5/0006; A61B 5/0205; A61B 5/029; A61B 5/04012; A61B 5/743; A61B 5/742; A61B 5/7239; A61B 5/0245; A61B 5/044; A61B 5/0456; A61B 5/0468; A61B 5/0004; A61B 5/024; A61B 5/0432; A61B 5/053; A61B 5/7282; G06F 19/345; G06F 19/321; G06F 19/3437; A61N 1/00
See application file for complete search history.

(56) References Cited

U.S. PATENT DOCUMENTS 5,309,917 A * 5/1994 Wang ................. A61B 5/04012
600/508

OTHER PUBLICATIONS

Brookes, et al., "Myocardial Contractility Is Not Constant During Spontaneous Atrial Fibrillation in Patients", Circulation (1998) vol. 98, p. 1762-1768, 8 pages.

(Continued)

*Primary Examiner* — Deborah Malamud
(74) *Attorney, Agent, or Firm* — Rankin, Hill & Clark LLP

(57) ABSTRACT

The present invention provides a method for creating and pathophysiologically analyzing graphs of cardiac function in atrial fibrillation and sinus arrhythmia by using thoracic impedance measurements. A two-dimensional scatter plot is created by applying (dZ/dt)min values corresponding to preceding RR interval (RR1) values and an approximate curve (i.e., cardiac function curve) is fitted to dots on the plot. The distribution pattern of the dots and the slope of the approximate curve allow for readily and visually evaluating cardiac function. Furthermore, a graph of the relationship between (dZ/dt)min values and RR1/pre-preceding RR interval (RR2) ratio values makes it possible to analyze pathophysiological mechanisms of cardiac function in more detail. This novel method of the present invention can be (Continued)

easily and repeatedly performed in atrial fibrillation and sinus arrhythmia with less of a physical burden on the patient, thereby being able to provide a very useful information for diagnosis and treatment.

14 Claims, 14 Drawing Sheets

(51) Int. Cl.
    *A61B 5/044*     (2006.01)
    *A61B 5/046*     (2006.01)
    *A61B 5/0432*     (2006.01)
    *A61B 5/0456*     (2006.01)
    *A61B 5/0468*     (2006.01)
    *A61B 5/053*     (2006.01)

(52) U.S. Cl.
    CPC ............ *A61B 5/046* (2013.01); *A61B 5/0432* (2013.01); *A61B 5/0456* (2013.01); *A61B 5/0468* (2013.01); *A61B 5/053* (2013.01)

(56) References Cited

OTHER PUBLICATIONS

Muntinga, et al., "Left Ventricular Beat to Beat Performance in Atrial Fibrillation: Dependence on Contractility, Preload and Afterload", Heart (1999), vol. 82, p. 575-580, 7 pages.

Schneider, et al., "Interval-Dependent Changes in Left Ventricular Contractile State in Lone Atrial Fibrillation and in Atrial Fibrillation Associated with Coronary Artery Disease", Am. J. Cardiol. (1997), vol. 80, p. 586-590, 5 pages.

Harley & Greenfield, "Determination of Cardiac Output in Man by Means of Impedance Plethysmography", Aerospace Medicine (1968), vol. 39 (3), p. 248-252, 5 pages.

* cited by examiner

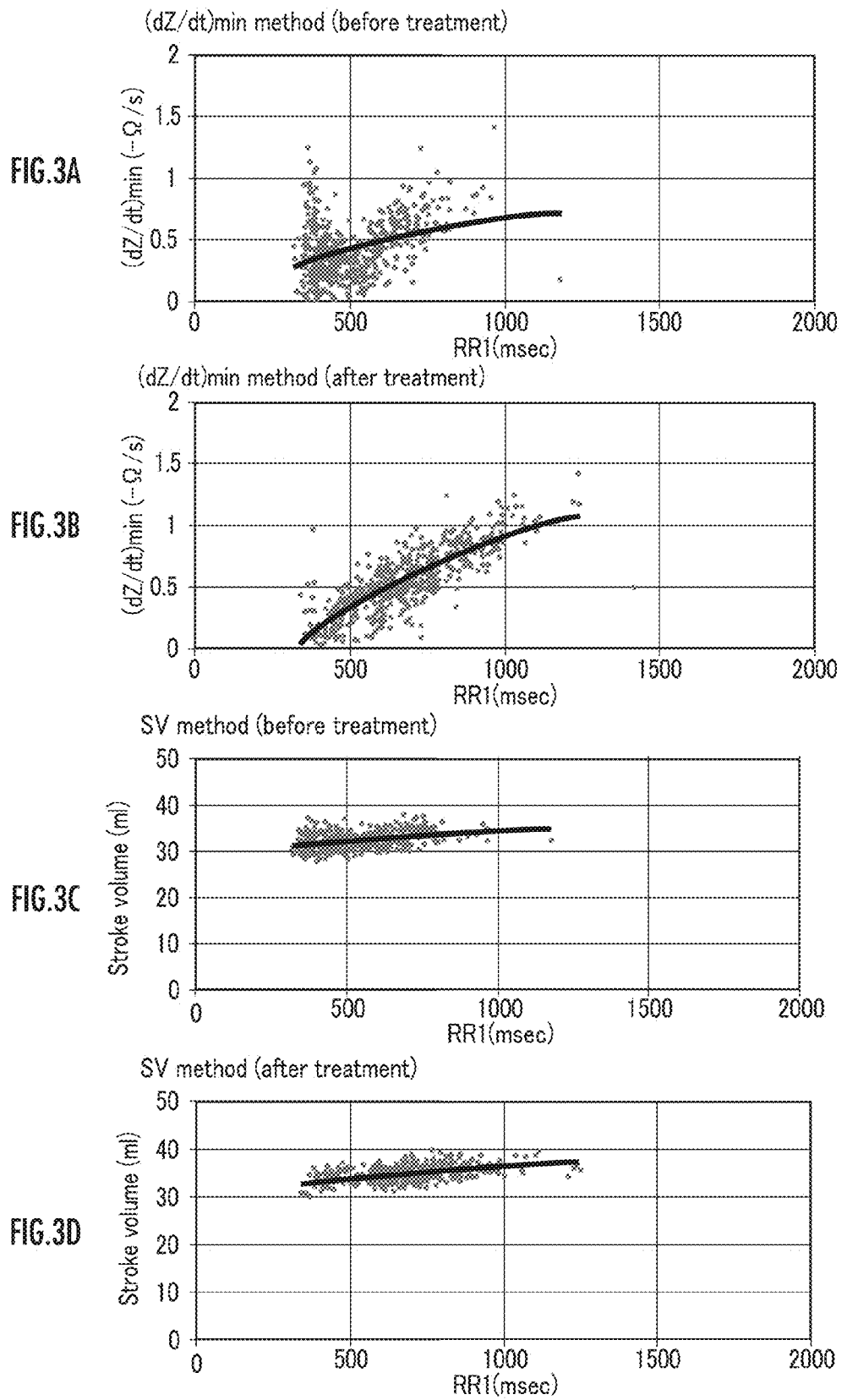

State of heart failure with atrial fibrillation

State of atrial fibrillation with well preserved cardiac function

State of sinus rhythm

FIG.6A
Postextrasystolic potentiation
RR1/RR2>1
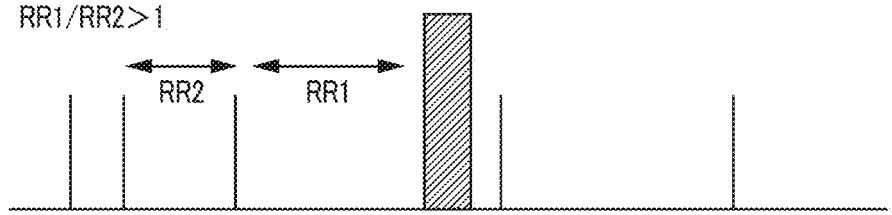
FIG.6B
Frank-Starling mechanism
RR1/RR2<1
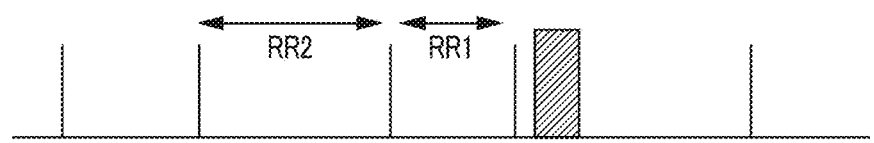
RR1/RR2=1
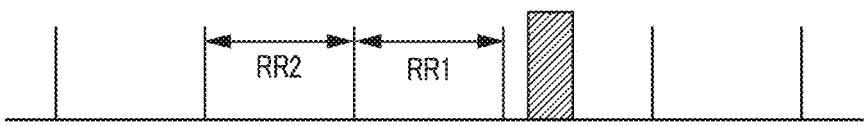

FIG.9A
FIG.9B
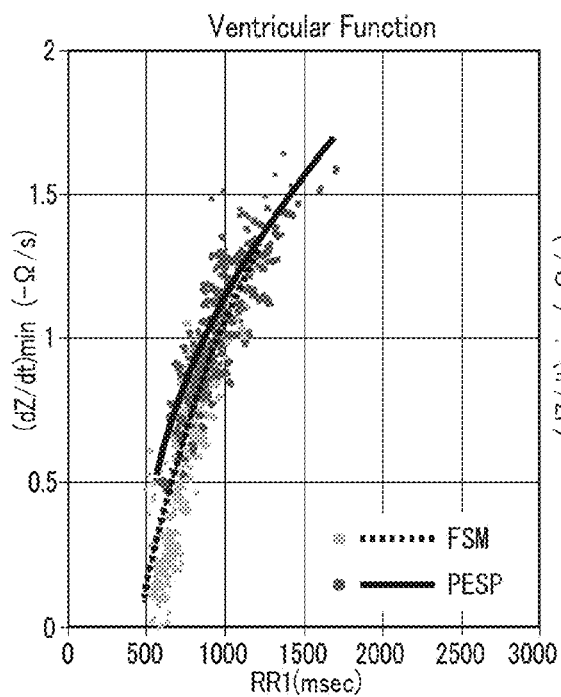
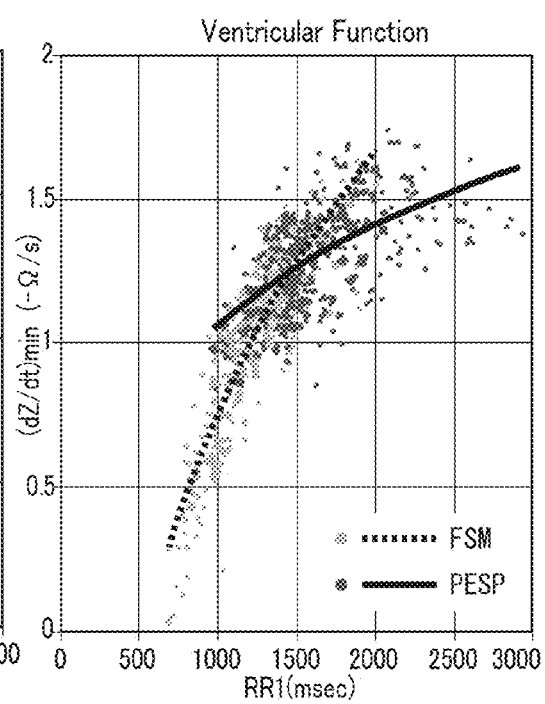
Before administration of digitalis
After administration of digitalis

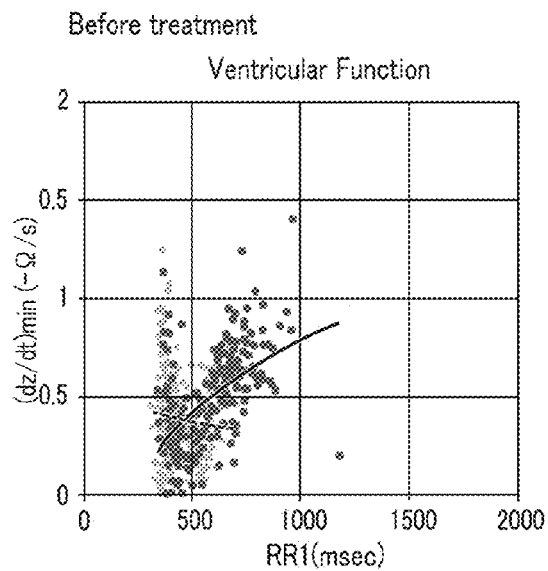
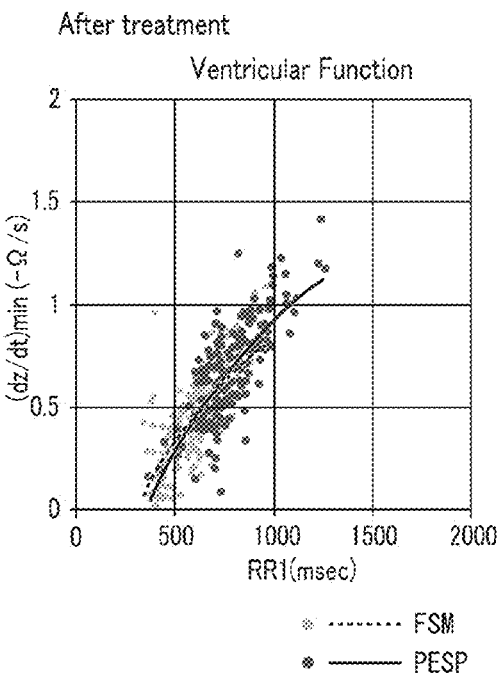
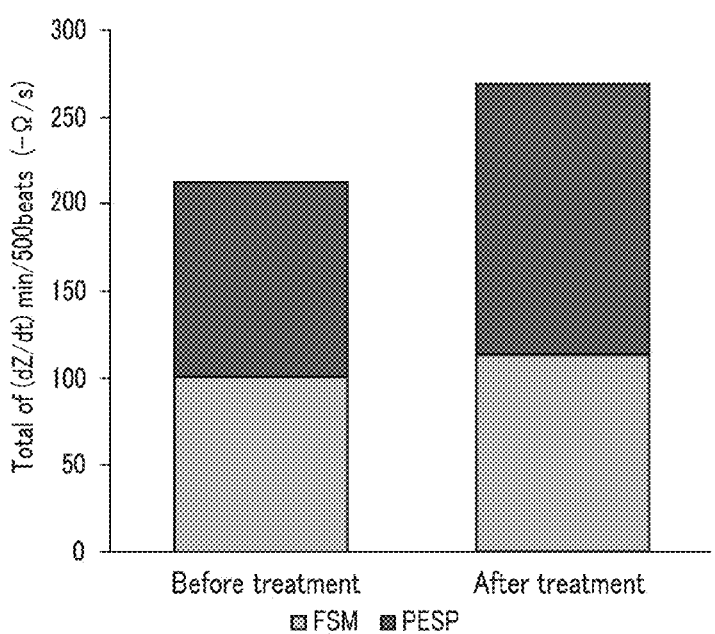

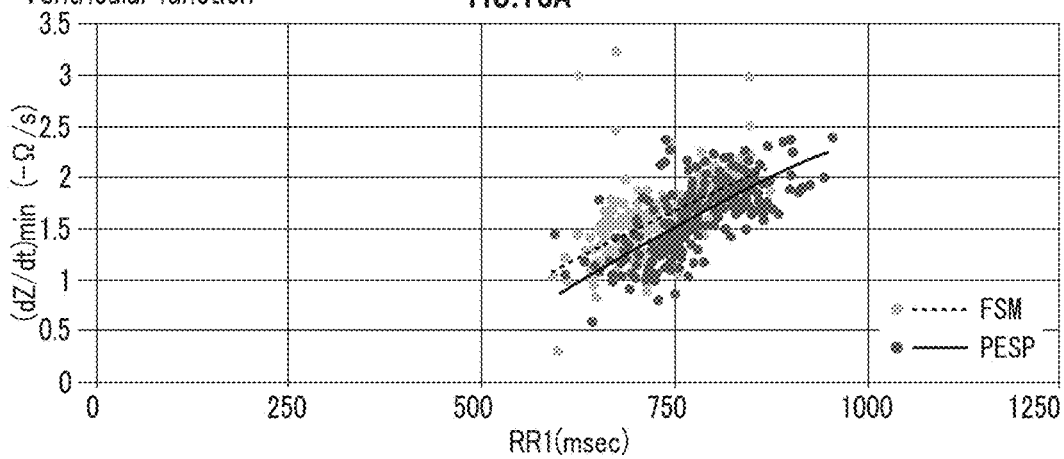
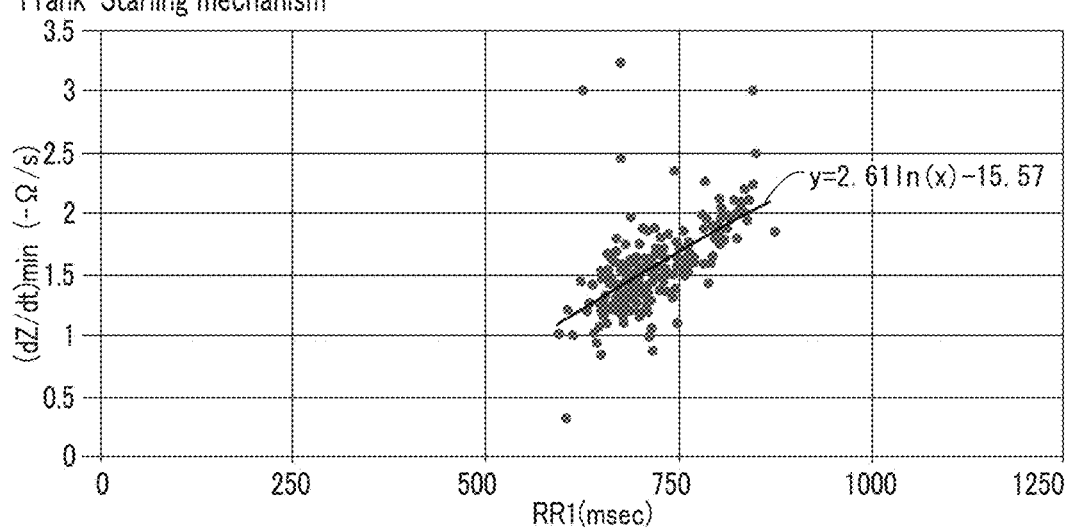
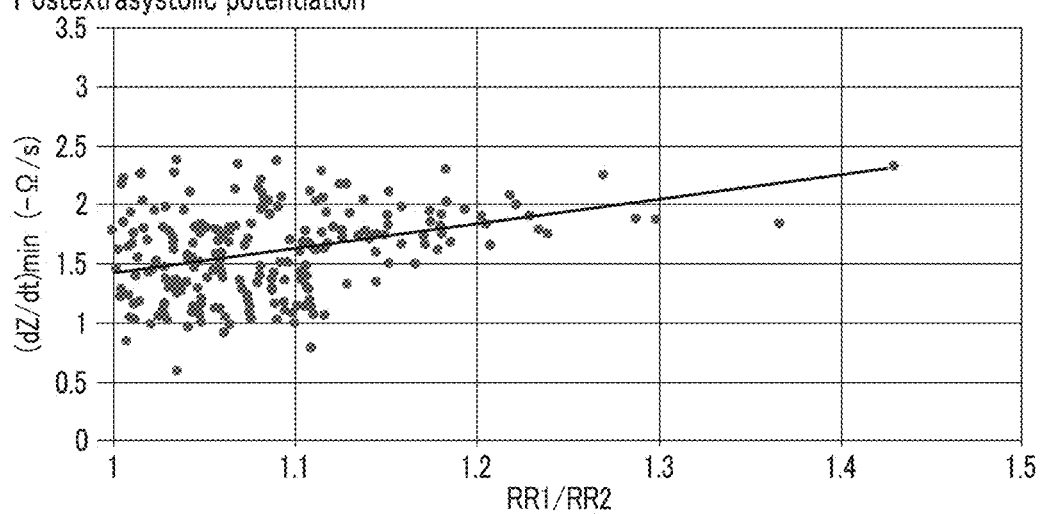

METHOD FOR CREATING AND ANALYZING GRAPHS OF CARDIAC FUNCTION IN ATRIAL FIBRILLATION AND SINUS ARRHYTHMIA BASED ON THORACIC IMPEDANCE MEASUREMENTS

TECHNICAL FIELD

The present invention provides a method for creating and analyzing graphs of cardiac function on the basis of thoracic impedance measurements in atrial fibrillation and sinus arrhythmia for objectively evaluating cardiac function, selecting a therapeutic medication, and estimating effects of treatment.

TECHNICAL BACKGROUND

An increase in cardiovascular disease is predicted in association with the aging society. Early detection and treatment of cardiovascular disease are important and a periodic examination of cardiovascular function is needed.

Morbidity of atrial fibrillation in cardiovascular disease is known to increase with aging, and epidemiological studies have shown that its prevalence rapidly increases in over the age of 70, and reached 4 to 8% in the seventies and 10% in the eighties. It has been indicated that patients with atrial fibrillation have a high risk for a left atrial thrombus, which flows out from the heart and occludes cerebral vessels to cause cardioembolic stroke. Accordingly, in recent years, aggressive treatment with anticoagulants for preventing cardioembolic stroke have dramatically improved treatment of cardiogenic brain embolism associated with atrial fibrillation.

On the other hand, the heart rhythm in atrial fibrillation is irregular and often results in tachycardia. Therefore, cardiac output is decreased and cardiac function is worsened. The heart rate control therapy in the irregular heart beat has been performed not to cause deterioration of cardiac function. However, the results of mega-clinical trial have demonstrated that there is no significant differences in life prognosis between the strict rate control group, in which patients have a heart rate of less than 80 beats per minute, and the lenient rate control group, in which patients have a heart rate of less than 110 beats per minutes. Consequently, it has been considered that it is not necessary for patients with atrial fibrillation to be treated on the basis of target heart rate. To date, medical treatment in atrial fibrillation is performed based on patient's complaints such as palpitation, shortness of breath, and general fatigue.

As rapidly increasing an aging population, patients with atrial fibrillation and dementia have similarly increased. Furthermore, it has been reported that risk of dementia in patients with atrial fibrillation was increased approximately 1.4-fold. Therefore, it is considered to be problematic for medical treatment on the basis of only elderly patient's complaints as well as complaints of pediatric patients who cannot appropriately explain symptoms. For these reasons, it has been needed to objectively diagnose, perform medical treatment, and observe response to treatment by using a reasonable index for assessment of cardiac function in atrial fibrillation instead of the therapeutic strategy based on subjective patient's complaints.

PRIOR ARTS LIST

Non-Patent Document 1: C. I. O. Brookes et al., Circulation (1998) Vol. 98, p. 1762-1768

Non-Patent Document 2: H. J. Muntinga, et al., Heart (1999), Vol. 82, p. 575-580

Non-Patent Document 3: F. Schneider et al., Am J Cardiol. (1997), Vol. 80, p. 586-590

Non-Patent Document 4: Harley & J. C. Greenfield Jr., Aerospace Medicine (1968), Vol. 39(3), p. 248-252

SUMMARY OF THE INVENTION

Problems to be Solved by the Invention

Traditionally, there have been known to be four representative cardiac function tests to obtain indices for assessment of cardiac function in atrial fibrillation, namely cardiac catheterization, cardiac radionuclide examination, echocardiography, and thoracic impedance method (see Non-Patent Documents 1 to 4). These examinations and their problems are briefly described below.

The cardiac catheterization is the most accurate and reliable test among cardiac function tests. However, it is a very invasive test in which a catheter is directly inserted into the aorta with administration of a contrast medium. Then, it cannot be performed easily and repeatedly for patients because of pain, bleeding, infection, and various other risk.

The cardiac radionuclide examination for evaluating cardiac function is also accurate, whereas a special examination room is required for using radioactive tracer and hospitals with that room are limited. Then, it cannot be also performed repeatedly for patients to assess therapeutic effects in clinical course due to the problem associated with exposure to radiation from radio-indicator.

Both the cardiac catheterization and the cardiac radionuclide examination require inpatient facilities and large medical devices. Thus, they are carried out in only limited hospitals and cannot be repeatedly performed in patients in clinical course due to the problem associated with exposure to radiation and a considerable physical burden on the patients.

The echocardiography can be noninvasively and readily carried out in a short period of time without large medical devices. However, this examination has several problems that cannot fully image the entire heart due to bones or air in the lung, and are dependent on the skill of the operators, which may be lead to differences in information processing. Thus, it is practically difficult to observe small changes in cardiac function in response to treatment and to follow them.

The thoracic impedance method is able to measure cardiac output noninvasively and repeatedly in a short period of time. Stroke volume (SV) measured by the thoracic impedance method has been used to evaluate cardiac function, while SV is considerably variable in atrial fibrillation. Consequently, the thoracic impedance method has not been used to evaluate cardiac function and to monitor response to treatment in atrial fibrillation for about 40 years.

To date, monitoring of cardiac function for medical treatment in patients with atrial fibrillation has not been performed sufficiently due to serious drawbacks in the above-described cardiac function tests.

An object of the present invention is to develop a method for evaluating cardiac function in atrial fibrillation, which can be carried out readily and repeatedly without a physical burden on the patient and has high sensitivity enough to observe small changes in cardiac function.

Another object of the present invention is to develop a method for analyzing measurement values of cardiac function in atrial fibrillation, which allows for easy and visual understanding of pathophysiological mechanisms of cardiac function and determination of selecting effective drugs based on the obtained measurement values without the need for any technique for measurements and analysis.

The inventor has found a novel highly sensitive method for evaluating cardiac function by creating a graph representing the peak flow velocity of blood ejected from the ventricles (hereinafter referred to as (dZ/dt)min) corresponding to preceding RR interval, both of which can be calculated by arithmetic processing of measurement values obtained using the thoracic impedance method, which is repeatedly and noninvasively capable of measurements without a physical burden on the patient.

Furthermore, the Frank-Starling mechanism (FSM) and postextrasystolic potentiation (PESP) are known as myocardial contractile mechanisms. The slope of the FSM curve represents the degree of contribution of three factors, namely preload, afterload, and myocardial contractility, and the slope of the PESP curve represents the myocardial contractile reserve.

The inventor has found a novel method for analysis of measurement values, which enables us to understand the pathophysiological mechanisms of cardiac function in more detail by evaluating the slope of the FSM curve and the PESP curve created by computing the relationship among (dZ/dt)min values, preceding RR interval values, and pre-preceding RR interval values.

According to the method of the present invention, patients with heart failure associated with atrial fibrillation can be readily and objectively detected, evaluated for the severity of the disease, selected for effective drugs, and assessed for effects of medical treatment. Therefore, it is possible to provide patients with heart failure and atrial fibrillation with more appropriate treatment.

Means to Solve the Problems

The present invention is related to a method for evaluating cardiac function, and is also related to a system and a program for executing the method, which is capable of comparing with a predefined model data to evaluate cardiac function. This method is as follows. (dZ/dt)min values corresponding to preceding RR interval (RR1) values, pre-preceding RR interval (RR2) values, and RR1/RR2 ratio values can be calculated from a large number of continuous thoracic impedance measurement values obtained by using means of measurements of cardiac function, and the results can be displayed on a scatter plot created by applying RR1 or RR1/RR2 ratio values to one axis, and (dZ/dt)min values to another axis.

Over the past years, it has never been displayed on a scatter plot created by applying (dZ/dt)min values to the y-axis, and beat-to-beat intervals, namely preceding RR interval (RR1) values and pre-preceding RR interval (RR2) values, to the x-axis, which were obtained from a large number of continuous thoracic impedance measurement values. The inventor has discovered that cardiac function can be evaluated by a scatter plot created by applying preceding RR intervals to one axis and the corresponding (dZ/dt)min values to another axis based on measurement values obtained from a patient, and has completed the present invention.

The present invention is related to a method for evaluating cardiac function, and is also related to a system and a program for executing the method, which is capable of comparing with a predefined model data to evaluate cardiac function. This method is as follows. (dZ/dt)min values and corresponding preceding RR interval (RR1) values can be obtained from a large number of continuous thoracic impedance measurement values, as mentioned above. A two-dimensional scatter plot can be created by applying RR1 values to the x-axis, and the corresponding (dZ/dt)min values to the y-axis.

The present invention of method for evaluating cardiac function enables us to detect heart failure associated with atrial fibrillation with high sensitivity based on the distribution pattern of dots on a two-dimensional scatter plot, and to monitor cardiac function.

The present invention is related to a method for evaluating cardiac function, and is also related to a system and a program for executing the method, which is capable of comparing with a predefined model data to evaluate cardiac function. This method is as follows. (dZ/dt)min values, preceding RR interval (RR1) values, and pre-preceding RR interval (RR2) values can be calculated from a large number of continuous thoracic impedance measurement values, as mentioned above. A two-dimensional scatter plot can be created by applying (dZ/dt)min values corresponding to RR1 values greater than RR2 values (see FIG. 6A) to the y-axis, and the RR1/RR2 ratio values corresponding to the (dZ/dt)min values to the x-axis. This two-dimensional scatter plot represents postextrasystolic potentiation (PESP).

The present invention is related to a method for evaluating cardiac function, and is also related to a system and a program for executing the method, which is capable of comparing with a predefined model data to evaluate cardiac function. This method is as follows. (dZ/dt)min values, preceding RR interval (RR1) values, and pre-preceding RR interval (RR2) values can be calculated from a large number of continuous thoracic impedance measurement values, as mentioned above. A two-dimensional scatter plot can be created by applying (dZ/dt)min values corresponding to RR1 values less than or equal to RR2 values (see FIG. 6B) to the y-axis, and the RR1 values corresponding to the (dZ/dt)min values to the x-axis. This two-dimensional scatter plot represents Frank-Starling mechanism not involved in postextrasystolic potentiation.

Furthermore, the present invention is related to a method for evaluating cardiac function, and is also related to a system and a program for executing the method, which is capable of comparing with a predefined model data to evaluate cardiac function. This method is as follows. (dZ/dt)min values, the corresponding preceding RR interval (RR1) values, and pre-preceding RR interval (RR2) values are obtained on the basis of a large number of continuous thoracic impedance measurement values. (dZ/dt)min values are selected as the values representing postextrasystolic potentiation when the RR1 value corresponding to (dZ/dt)min value is greater than corresponding RR2 value (see FIG. 6A), and (dZ/dt)min values are selected as the values representing the Frank-Starling Mechanism that do not involve postextrasystolic potentiation when the RR1 value corresponding to (dZ/dt)min value is the same as or less than corresponding RR2 value (see FIG. 6B), a set of the selected (dZ/dt)min values representing postextrasystolic potentiation and the corresponding RR1 values, and another set of the selected (dZ/dt)min values representing the Frank-Starling Mechanism that do not involve postextrasystolic potentiation and the corresponding RR1 values are displayed so as to be identifiably superimposed as two sets of data in a two-dimensional scatter plot in which RR1 is used to the X-axis and (dZ/dt)min is used to the Y-axis in the two-dimensional scatter plot.

The method of the present invention enables us to evaluate cardiac function by using the identifiably superimposed (dZ/dt)min values representing postextrasystolic potentiation and (dZ/dt)min values representing the Frank-Starling mechanism.

The present invention can provide clinicians with detailed information about pathophysiological mechanisms in patients with atrial fibrillation by using the identifiably superimposed two-dimensional scatter plot representing postextrasystolic potentiation and the Frank-Starling mechanism. This is very useful for clinicians to select a therapeutic medication and to monitor response to treatment.

The present invention is related to a method for evaluating cardiac function, and is also related to a system and a program for executing the method, which is capable of comparing with a predefined model data to evaluate cardiac function. This method is as follows. Preceding RR interval (RR1) values, pre-preceding RR interval (RR2) values, and RR1/RR2 ratio values can be calculated from a large number of continuous thoracic impedance measurement values, as mentioned above. (dZ/dt)min values are selected as the values representing postextrasystolic potentiation when the RR1 value corresponding to (dZ/dt)min value is greater than corresponding RR2 value (see FIG. 6A), and (dZ/dt)min values are selected as the values representing the Frank-Starling Mechanism that do not involve postextrasystolic potentiation when the RR1 value corresponding to (dZ/dt)min value is the same as or less than corresponding RR2 (see FIG. 6B), then a set of the selected (dZ/dt)min values representing postextrasystolic potentiation and the corresponding RR1 values and RR1/RR2 ratio values, and another set of the selected (dZ/dt)min values representing the Frank-Starling Mechanism that do not involve postextrasystolic potentiation and the corresponding RR1 values and RR1/RR2 ratio values are displayed so as to be identifiably superimposed as two sets of data in a three-dimensional scatter plot in which RR1 is used to the X-axis, RR1/RR2 is used to the Y-axis, and (dZ/dt)min is used to the Z-axis.

This three-dimensional scatter plot enables us to readily and identifiably evaluate differences in the distribution of dots in postextrasystolic potentiation and the Frank-Starling mechanism, and to observe small changes in cardiac function by separating overlapping dots which might be visually difficult to evaluate.

Moreover, the present invention is related to a method for evaluating cardiac function, and is also related to a system and a program for executing the method, which is capable of comparing with the thoracic impedance measurement values of different periods in a same patient. This method is as follows. The display of identifiably superimposed thoracic impedance measurement values of different periods in a same patient can be compared with a predefined model data.

Displaying identifiably superimposed measurement values of different periods in a same patient enables us to accurately evaluate changes in deterioration of a disease and response to treatment, and thereby to determine selection of effective drugs on the basis of objective measurement values.

The present invention is related to a method for evaluating cardiac function, and is also related to a system and a program for executing the method, in which an approximate curve is used. This method is as follows. An approximate curve calculated using measurement values from a scatter plot can be superimposed on the scatter plot, or measurement values can be displayed by the approximate curve alone to evaluate cardiac function.

Calculating a slope of an approximate curve fitted to a scatter plot can present a numerical index in addition to the distribution pattern of the scatter plot. Thus, this objective index is very useful for clinicians to evaluate cardiac function.

The present invention is related to a method for evaluating cardiac function, and is also related to a system and a program for executing the method, in which the sum of (dZ/dt)min values in postextrasystolic potentiation can be compared with the sum of (dZ/dt)min values in Frank-Starling mechanism. This method is as follows. Preceding RR interval (RR1) values, and pre-preceding RR interval (RR2) values can be obtained from a large number of continuous thoracic impedance measurement values, as mentioned above. (dZ/dt)min values corresponding to RR1 values greater than RR2 values as a plot of postextrasystolic potentiation (see FIG. 6A), and (dZ/dt)min values corresponding to RR1 values less than or equal to RR2 values as a plot of Frank-Starling mechanism (see FIG. 6B) can be obtained according to the relationship between RR1 values and RR2 values. The sum of (dZ/dt)min values in postextrasystolic potentiation can be compared with the sum of (dZ/dt)min values in Frank-Starling mechanism to evaluate cardiac function.

This method enables us to quantify the degree of involvement of postextrasystolic potentiation and the Frank-Starling mechanism in pathophysiological mechanisms of cardiac function, which is capable of providing very useful information to monitor response to treatment.

BRIEF DESCRIPTION OF THE DRAWINGS

FIG. 3 shows two-dimensional scatter plots created by using thoracic impedance measurement values in a same case, where FIG. 3A is before treatment and FIG. 3B is after treatment, both of which are shown by using the (dZ/dt)min method of the present invention, FIG. 3C is before treatment and FIG. 3D is after treatment, both of which are shown by using the conventional SV method;

FIG. 4 shows graphs of cardiac function based on simultaneous measurements using thoracic impedance method and echocardiography, where both

FIG. 6A represents postextrasystolic potentiation and FIG. 6B represents the Frank-Starling mechanism based on the relationship between preceding RR interval (RR1) and pre-preceding RR interval (RR2);

FIG. 9 shows changes in the relationship between Frank-Starling curve and postextrasystolic potentiation curve, where FIG. 9A shows before administration of digitalis and FIG. 9B shows after administration of digitalis;

FIG. 11 shows the changes in the relationship between the Frank-Starling curve and postextrasystolic potentiation curve, where FIG. 11A shows before treatment and FIG. 11B shows on the way to treatment of heart failure, and FIG. 11C shows the sum of the degree of involvement of each pathophysiological mechanism;

FIG. 13 shows a case of a pediatric patient with respiratory sinus arrhythmia, which the present invention has been applied to except for atrial fibrillation, where FIG. 13A indicates a two-dimensional scatter plot simultaneously representing Frank-Starling mechanism and postextrasystolic potentiation, FIG. 13B indicates the Frank-Starling mechanism curve, and FIG. 13C indicates postextrasystolic potentiation curve.

DESCRIPTION OF THE EMBODIMENTS

The inventor has found that cardiac function in patients with atrial fibrillation can be readily evaluated with high sensitivity by displaying measurement values analyzed using a novel analytical method, which can be obtained noninvasively using thoracic impedance method without a physical burden on the patient. A conventional stroke volume method for evaluating cardiac function using thoracic impedance is described below with the drawings. Then, embodiments of the present invention are subsequently described in detail.

The cardiac cycle is composed of a systole and a diastole. Diastole is characterized by increasing the ventricular cavity of both left and right ventricles. Blood flows from both left and right atrium into each ventricle, resulting in ventricular filling. Systole is characterized by ejecting blood from each ventricle to the aorta and pulmonary artery. The R wave, which is highest in upward spikes of an electrocardiogram, appears during the systole (see FIG. 2). Blood is ejected from the ventricles during a cardiac cycle (i.e., an interval between an R wave and the following R wave) consisting of a systole and a diastole. In an electrocardiogram, the ventricular systole corresponds to the interval from the R wave to the end of the T wave, and the ventricular diastole corresponds to the interval from the end of the T wave to the following R wave. The interval between an R wave and the following R wave in an electrocardiogram is called the RR interval (see FIG. 1 and FIG. 2).

Figure 1A:
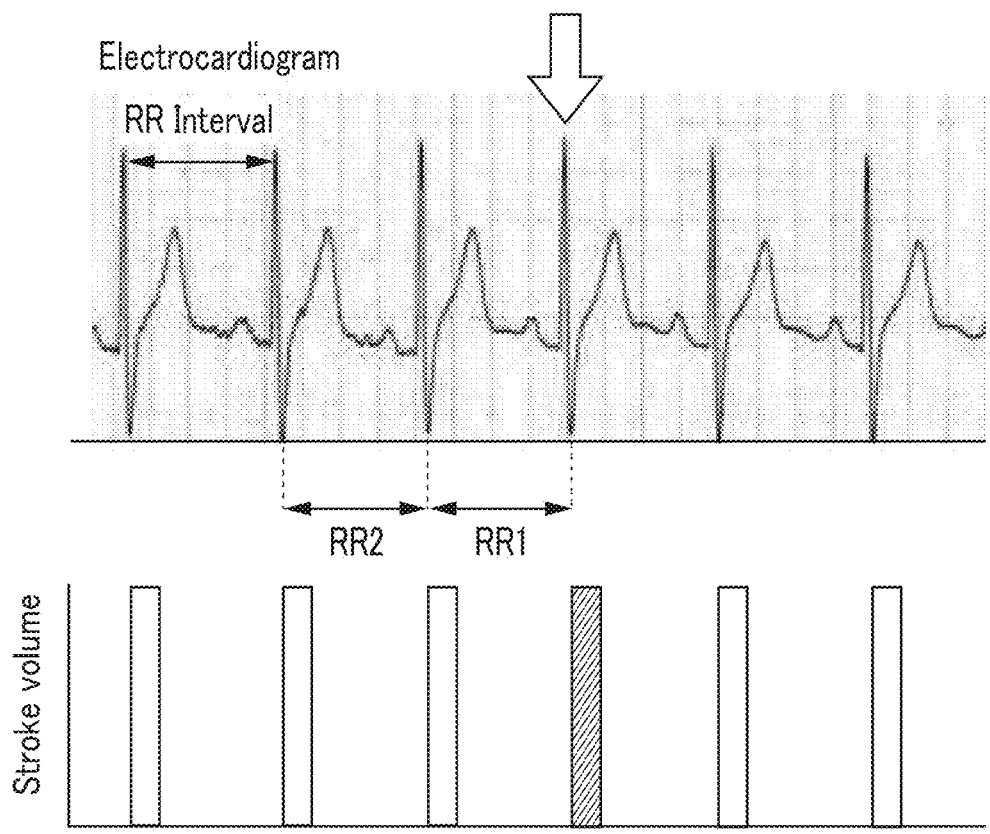
FIG. 1A schematically shows the relationship among a preceding RR interval (RR1), a pre-preceding RR interval (RR2) of an electrocardiogram, and a stroke volume.

In accordance with constant intervals of cardiac cycle, RR intervals are also constant. FIG. 1A shows an electrocardiogram of a patient with regular sinus rhythm. As shown in FIG. 1A, when keeping regular sinus rhythm, beat-to-beat intervals are held constant and systolic and diastolic time intervals are also constant. Thus, the stroke volume is constant because of constant blood volume of ventricular inflow and outflow. Then, the RR interval of immediately prior to the onset of ejection of blood from the heart is called the preceding RR interval (RR1). FIG. 1A schematically shows the relationship between RR1 of immediately prior to the R wave indicated by an arrow and the stroke volume corresponding to the RR1 (indicated by hatched bar).

Figure 1B:
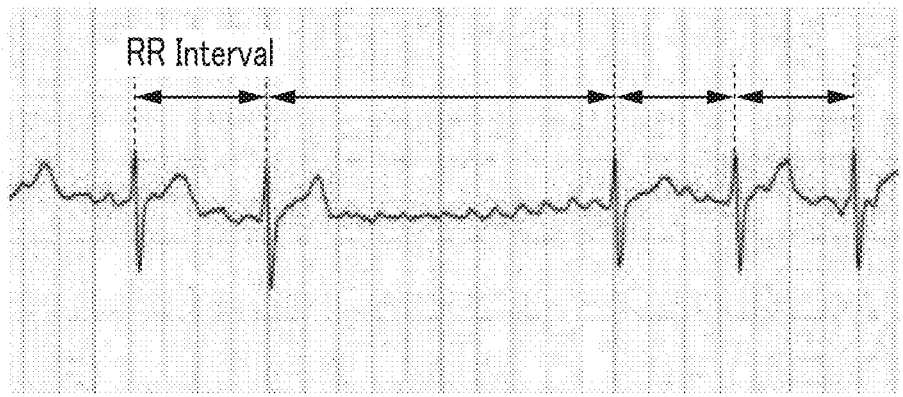
FIG. 1B shows an electrocardiogram in a patient with atrial fibrillation.

In atrial fibrillation, however, RR intervals are irregular. FIG. 1B shows an electrocardiogram of a patient with atrial fibrillation, and cardiac cycle is not constant in accordance with apparent variation in RR intervals.

Generally, when a preceding RR interval (RR1) is long, the diastolic time interval is likely to be prolonged, resulting in an increased blood volume in the ventricles due to increasing duration of blood flow from atria into ventricles. Consequently, the volume of blood ejected from the ventricles is also increased during systole. In contrast, when a preceding RR interval is short, the diastolic time interval is likely to be shortened, resulting in a decreased blood volume in the ventricles due to decreasing duration of blood flow from atria into ventricles. Consequently, the volume of blood ejected from the ventricles is also decreased during systole.

Based on this physiological mechanism, a graph of cardiac function has been generated by applying stroke volume (SV) values or similar indices to the y-axis against preceding RR interval (RR1) values on the x-axis to evaluate cardiac function in patients with atrial fibrillation by using noninvasive examinations. SV can be obtained by using thoracic impedance method as described below.

Figure 2:
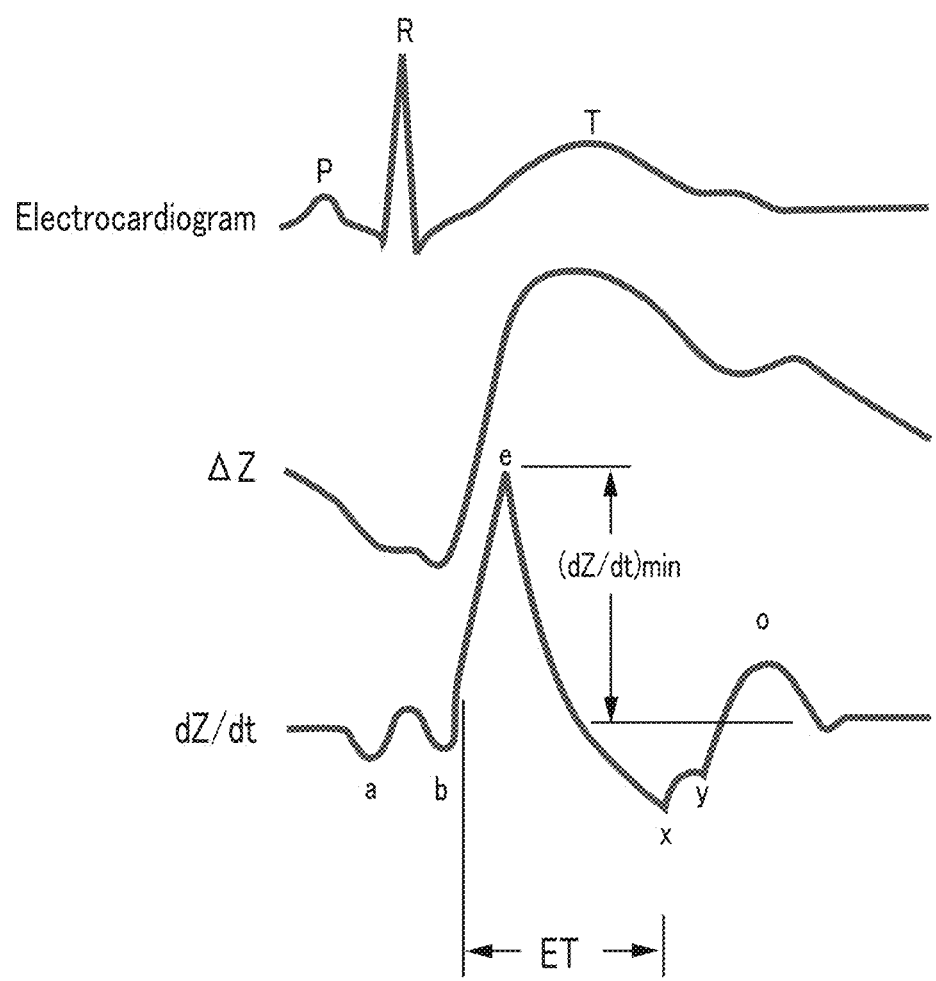
FIG. 2 shows an electrocardiogram, changes in thoracic impedance (ΔZ) associated with a heartbeat, and the first derivative of the thoracic impedance waveform (dZ/dt)

The thoracic impedance method is summarized as follows. FIG. 2 shows changes in thoracic impedance: ΔZ, and the first derivative of ΔZ signal: dZ/dt associated with a normal heartbeat. In thoracic impedance method, two pairs of band electrodes are placed around the neck and the below the xiphoid process. A high-frequency electric current is passed through between the outer two electrodes and the changes in voltage can be detected between the inner two electrodes. Thus, thoracic impedance method is a noninvasively and readily available method.

As shown in FIG. 2, a, b, e, x, y, and o waves are observed in dZ/dt signal. A-wave is associated with the atrial contraction, b-wave is associated with the onset of ejection of blood from the ventricles to the arteries, e-wave, namely (dZ/dt)min, is associated with the peak flow velocity of blood ejected from the ventricles, x-point corresponds to the closure of the aortic valve, y-point corresponds to the closure of pulmonic valve, and o-wave is associated with opening snap of mitral valve. Then, a-wave is not observed in atrial fibrillation because of a loss of atrial contraction.

In addition, the ejection of blood from the ventricles during systole leads to a decrease in the thoracic impedance, which is recorded as a downward deflection ($-\Omega/s$). In general, the phase is inverted to help better visual recognition of the relationship with hemodynamics, and the phase is displayed in an inverted manner in the present invention as well.

The stroke volume (SV) is calculated using the following Kubicek formula from measurement values obtained by the thoracic impedance method:

$$SV = \rho (L/Zo)^2 (dZ/dt)\text{min} \times ET$$

[where $\rho$ is blood resistivity ($\Omega \times cm$), ET is left ventricular ejection time (sec), L is distance between receiving electrodes, and Zo is thoracic baseline impedance]

The thoracic impedance method is a technique to readily and noninvasively evaluate cardiac function and is clinically useful. This is because stroke volume (SV) values obtained using thoracic impedance technique in patients with regular sinus rhythm are correlated well with those obtained using different methods to invasively assess cardiac function.

In patients with atrial fibrillation, a signal to noise ratio (S/N) of (dZ/dt)min and left ventricular ejection time become lower, because the changes in thoracic impedance, ΔZ, corresponding to heart beats become smaller. Consequently, SV values calculated by multiplying (dZ/dt)min and ET together, both of which are low S/N ratio, using the Kubicek formula would cause a large error in those values in patients with atrial fibrillation. For these reasons, stroke volume values obtained using thoracic impedance technique have not been considered to appropriately reflect cardiac function in patients with atrial fibrillation.

The inventor has found the importance of the (dZ/dt)min among parameters related to cardiac function, which are obtained using thoracic impedance method, in patients with atrial fibrillation. The (dZ/dt)min is the first derivative of ΔZ, which represents the peak flow velocity of blood ejected from the ventricles and is associated with ventricular contractility. Then, the inventor has developed a novel method for evaluating cardiac function in patients with atrial fibrillation by means of using a graph of cardiac function created by applying the (dZ/dt)min values to the y-axis and has completed the present invention. When using this method, even in the presence of atrial fibrillation, patients can be readily and noninvasively evaluated for cardiac function by using thoracic impedance method. The method of the present invention is described below using embodiments, but the scope of the present invention is not limited thereby.

Embodiment 1

Method for Displaying a Two-Dimensional Scatter Plot

A patient is attached to a thoracic impedance device and 500 consecutive heart beats are recorded. The time required for measurements is 7 to 10 minutes. Preceding RR intervals and the corresponding (dZ/dt)min values are calculated from thoracic impedance measurement values.

The method of the present invention described here mainly uses a trans-thoracic impedance device. Whichever can be used as an impedance device, however, if allowing to measure thoracic impedance. For example, impedance measurement values may be obtained by using implantable pacemaker with intra-thoracic impedance device.

In this embodiment, 500 consecutive heart beats are measured, whereas a statistically reliable number of heart beats may allow for evaluating cardiac function in a shorter time.

From obtained measurement values, a two-dimensional scatter plot is created by applying preceding RR interval (RR1) values to the x-axis, and the corresponding (dZ/dt)min values to the y-axis. Furthermore, an approximate curve (a logarithmic regression curve) is calculated using measurement values from the scatter plot.

An example is shown in FIG. 3. FIG. 3A shows thoracic impedance measurement values displayed by the (dZ/dt)min method of the present invention in a patient with heart failure before treatment. FIG. 3C is a two-dimensional scatter plot with an approximate curve displayed by the conventional stroke volume (SV) method for evaluating cardiac function, which uses RR1 values and the corresponding SV values as coordinates, in the same patient with heart failure before treatment.

As shown in FIG. 3A, the distribution of dots displayed a V-shaped pattern on the two-dimensional scatter plot using RR1 values and the corresponding (dZ/dt)min values as coordinates. This distribution pattern of dots are often observed associated with deterioration of heart failure, which has been discovered by the method of the present invention. Dots distributed characteristically in a belt-like area extending vertically in RR intervals ranging from 400 to 500 ms mainly represent heart beats associated with attenuation of the Frank-Starling mechanism.

FIG. 3B is a graph created by the method of the present invention after treatment. Dots distributed characteristically in a belt-like area extending vertically in RR intervals ranging from 400 to 500 ms, which was shown in FIG. 3A and associated with deterioration of heart failure, apparently disappeared and the slope of the approximate curve markedly shifted upward. In this way, when using the method of the present invention, the distribution pattern of dots on a two-dimensional scatter plot varies in different stages of the disease, thereby allowing to use as an indicator of the severity of the disease.

In contrast, FIG. 3D is a two-dimensional scatter plot using stroke volume (SV) values and the corresponding RR1 values as coordinates in the same patient with heart failure and atrial fibrillation after treatment. Evaluating effects of treatment is difficult due to little differences in the distribution patterns of dots and the slope of the approximate curves on the two-dimensional scatter plots between before treatment in FIG. 3C and after treatment in FIG. 3D.

Therefore, the (dZ/dt)min method of the present invention is capable of evaluating small changes in cardiac function in response to treatment with higher sensitivity compared to the conventional SV method in patients with atrial fibrillation.

Subsequently, the method of the present invention using (dZ/dt)min was compared with another noninvasive method using echocardiography.

Figure 4A:
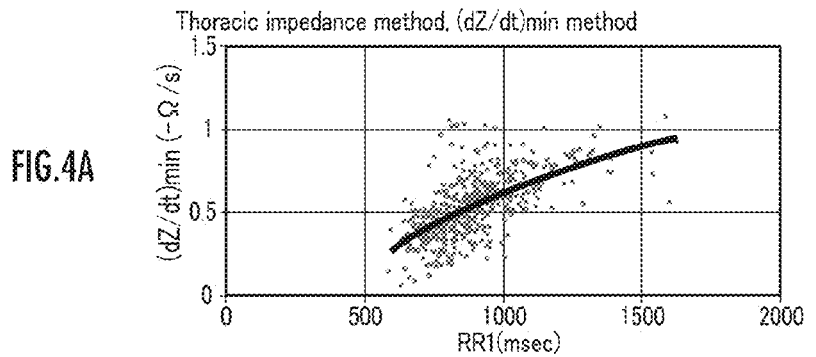
FIG. 4A and FIG. 4B are shown by using thoracic impedance method, however, the former is shown by using the (dZ/dt)min method of the present invention and the latter is shown by using the conventional analytic method.
Figure 4B:
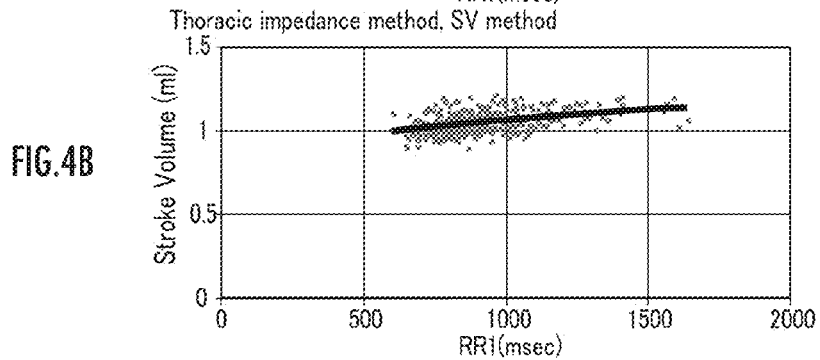
Figure 4C:
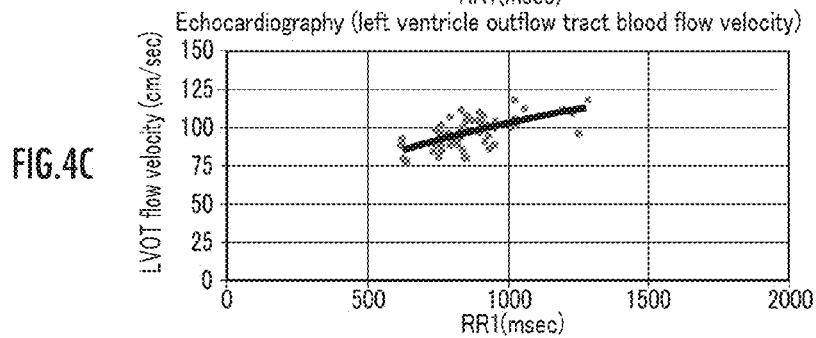
FIG. 4C is shown by using echocardiography.

FIG. 4A is a graph shown by applying (dZ/dt)min values obtained using thoracic impedance method of the present invention against the corresponding preceding RR interval (RR1). FIG. 4B is a graph shown by applying SV values obtained using the conventional method for evaluating cardiac function to the y-axis against the corresponding RR1. FIG. 4C is a graph representing the relationship between RR1 values and peak flow velocity values in the left ventricle outflow (LVOT flow velocity) in the 65 consecutive heart beats measured by echocardiography.

Sensitivity of the three graphs shown in FIG. 4A to FIG. 4C couldn't be directly compared, because of differences in ordinate unit of each graph. Using an adjusted unit of measurements described below, the sensitivity to changes in preceding RR interval (RR1) values were compared among them.

The increases in the y-value per 1 msec increment in RR1 on the x-axis ($Y_{n+1}-Y_n$ per 1 msec) were calculated using the approximate curves of the three graphs. The average value of the y-values corresponding to the RR1 values of each graph was calculated, and the ratios of the increments in $Y_{n+1}-Y_n$ to the average value were obtained for comparison of the sensitivity.

Figure 4D:
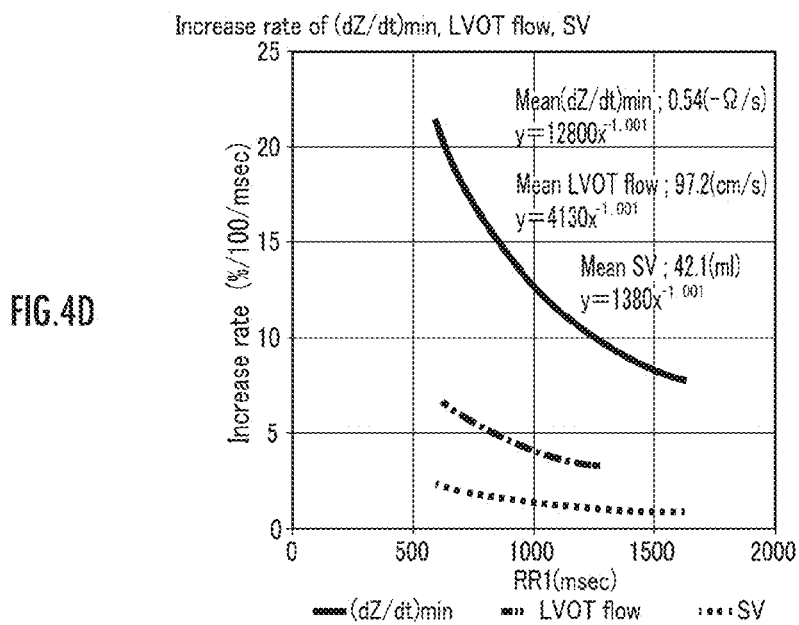
FIG. 4D shows differences in sensitivity of these three graphs represented by using an adjusted unit of measurements.

FIG. 4D shows exponential curves adjusted as described above. The sensitivity of the (dZ/dt)min method of the present invention to changes in RR1 intervals was approximately 9-fold higher than the conventional SV method and about 3-fold higher than the method using LVOT flow velocity measured by echocardiography. Thus, this method of the present invention has been sufficiently confirmed to allow for evaluating small changes in the severity of the disease and cardiac function in response to treatment, which are required for clinically useful graphical method.

As described above, the (dZ/dt)min method of the present invention is very sensitive to small changes in disease, which allows for estimating changes in cardiac function by the distribution pattern of dots on a two-dimensional scatter plot (see FIGS. 3A and 3B). The thoracic impedance data obtained from many patients with atrial fibrillation were collected to analyze changes in cardiac function on the basis of the distribution pattern of dots on the two-dimensional scatter plot. These results revealed that changes in cardiac function could be estimated by the distribution pattern of dots on the two-dimensional scatter plot. FIG. 5 schematically shows that changes in cardiac function can be assessed by the distribution pattern of dots on the two-dimensional scatter plot created by using the (dZ/dt)min method of the present invention.

Figure 5A:
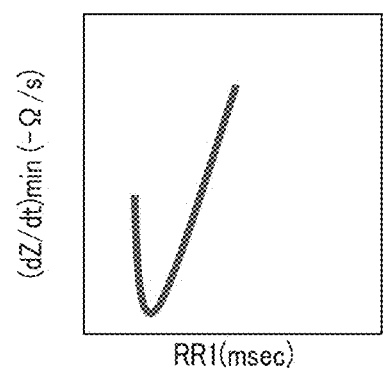
FIG. 5 schematically shows typical cardiac function represented by a two-dimensional scatter plot using the (dZ/dt)min method.
Figure 5B:
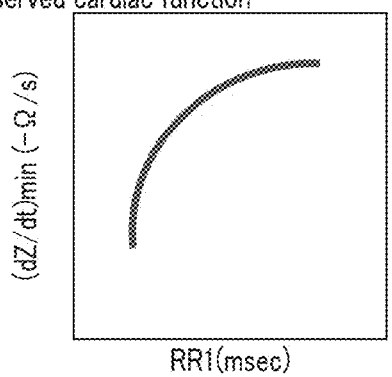

FIG. 5A schematically shows a representative distribution pattern of dots in heart failure with atrial fibrillation. The pattern of dots displays a V-shaped. FIG. 5B schematically shows a representative distribution pattern of dots on the two-dimensional scatter plot in patients with atrial fibrillation and well preserved cardiac function. The distribution pattern of dots shifts from the V-shaped area to the right upward curve on the two-dimensional scatter plot when cardiac function is improved. In addition, the dots are redistributed in a wide range of the x-axis because of prolonged RR intervals associated with the improvement in tachycardia.

Figure 5C:
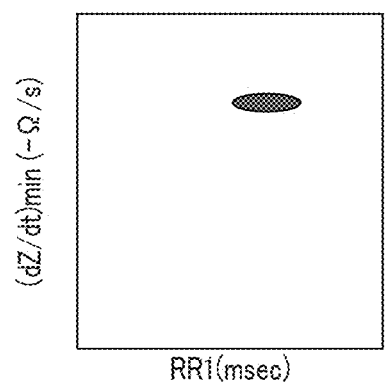

FIG. 5C schematically shows a representative distribution pattern of dots in patients with sinus rhythm. In the case of sinus rhythm, the RR intervals are relatively constant and the dots are localized to a small area.

In this way, cardiac function can be estimated by the distribution of dots on a two-dimensional scatter plot.

Embodiment 2

Method for Analyzing Measurement Values for the Postextrasystolic Potentiation (PESP)

As shown in FIG. 6A, thoracic impedance measurement values of a total of 500 consecutive heart beats were obtained from a patient with atrial fibrillation. A two-dimensional scatter plot was created by applying (dZ/dt)min values corresponding to preceding RR interval (RR1) values greater than pre-preceding RR interval (RR2) values, i.e., RR1/RR2>1, to the y-axis, and the corresponding RR1/RR2 ratio values to the x-axis. An approximate line was calculated using measurement values. The approximate line representing PESP line, was used by superimposed on the two-dimensional scatter plot or by the approximate line alone.

Figure 7A:
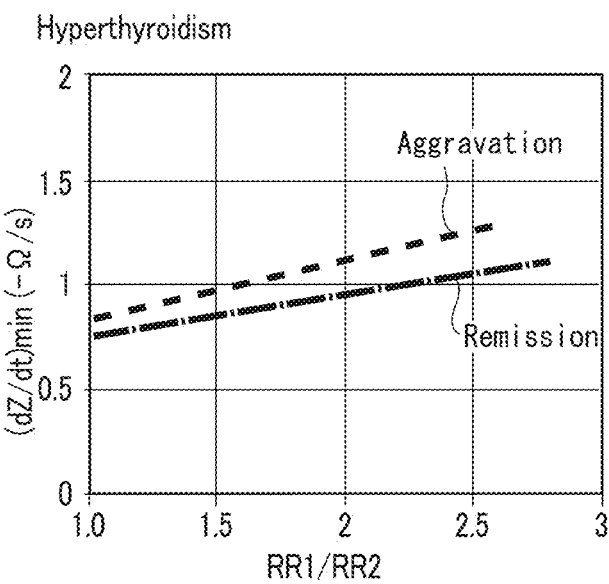
FIG. 7A shows hyperthyroidism and FIG. 7B shows administration of β-blocker, both of which affect the slope of the postextrasystolic potentiation curves.

FIG. 7 is example showing by the approximate line alone. FIG. 7A shows postextrasystolic potentiation in a patient with hyperthyroidism and chronic atrial fibrillation, where a dashed-dotted line represents remission and the other dotted line represents aggravation of hyperthyroidism. Symptoms in patients with hyperthyroidism are associated with sympathetic overactivity such as palpitations, tachycardia, sweating, finger tremor, and the like. It is visually apparent that the slope of the line representing aggravation (dotted line) is greater than the slope of the line (dashed-dotted line) representing remission.

Figure 7B:
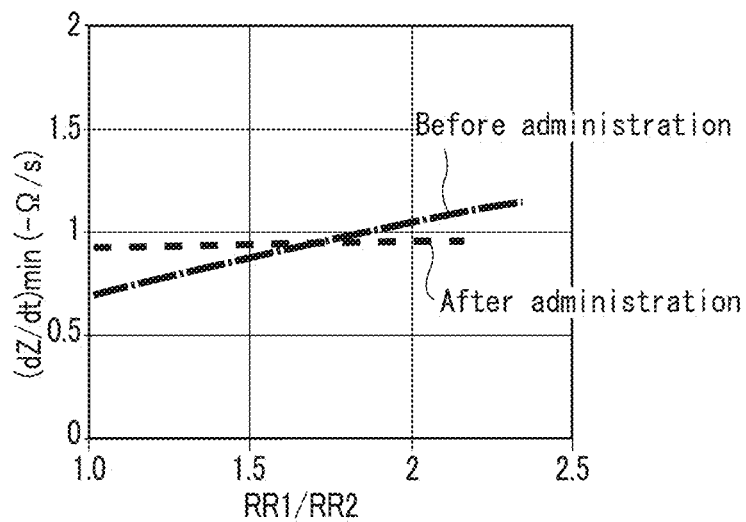

FIG. 7B is a graph showing β-blocker administration which reduces cardiac sympathetic activity in a patient with chronic atrial fibrillation, where the dashed-dotted line and the dotted line represent before and after administration of β-blocker respectively.

The slope of the dashed-dotted line was decreased after administration of β-blocker (i.e., that is shown by the dotted line associated with a decrease in the slope).

Time-frequency analysis of heart rate variability has been used as a clinical noninvasive method for evaluating the sympathetic activity, in which ratio of low-frequency power around 0.1 Hz to high-frequency power around 0.25 Hz, LF/HF ratio, has been proposed as a measure of sympathetic activity. This method allows for analysis of patients with sinus rhythm, whereas that cannot be used in patients with atrial fibrillation. The inventor has found that the slope of the approximate line on the two-dimensional scatter plot of PESP can be used as an indicator of sympathetic activity in patients with atrial fibrillation in addition to a conventional indicator of myocardial contractile reserve, as shown in FIG. 7. Therefore, the analytical method of the present invention makes it possible to visually evaluate the degree of sympathetic activity before and after treatment.

The present invention has enabled us to visually evaluate the degree of sympathetic activity in patients with atrial fibrillation for the first time by using the slope of the approximate line of the PESP.

Embodiment 3

Method for Analyzing Measurement Values for the Frank-Starling Mechanism (FSM)

As shown in FIG. 6B, thoracic impedance measurement values of a total of 500 consecutive heart beats were obtained from a patient with atrial fibrillation. A two-dimensional scatter plot was created by applying (dZ/dt)min values corresponding to preceding RR interval (RR1) values less than or equal to pre-preceding RR interval (RR2) values, i.e., RR1/RR2≤1, to the y-axis in order to completely eliminate the involvement of PESP, and the corresponding RR1 values to the x-axis. An approximate curve (i.e., logarithmic regression curve) was calculated. The Frank-Starling curve was represented by the approximate curve superimposed on the two-dimensional scatter plot or by the approximate curve alone. The Frank-Starling curve obtained in this way tends to be affected by three factors, namely preload, afterload, and myocardial contractility. Preload is the volume of blood which flows into ventricles during diastole. Afterload is the load experienced by the ventricles such as systemic arteriolar resistance when blood is ejected from the ventricles during systole. Some specific examples are described below with reference to FIG. 8.

(1) Influence of Preload

Figure 8A:
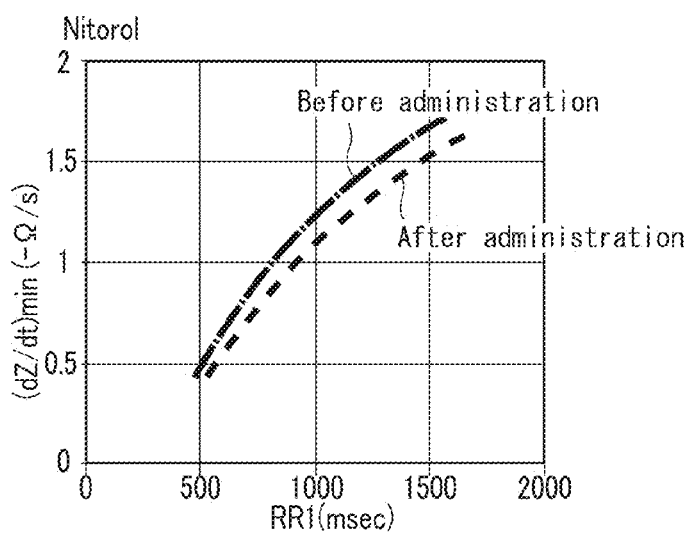
FIG. 8A shows administration of nitrate.

FIG. 8A shows a patient with dilated cardiomyopathy and chronic atrial fibrillation treated with intravenous injection of Nitorol (registered trademark). The approximate dashed-dotted curve represents before administration of Nitorol and the dotted curve represents after administration of Nitorol.

Patients with dilated cardiomyopathy experience symptoms such as dyspnea, cold sweating, and fatigue, associated with pulmonary congestion due to inadequate cardiac reserve during exercise.

Nitorol dilates venous capacitance vessels, which results in the accumulation of blood in the veins and a decrease in venous return (reduction in preload) for preventing progression of pulmonary congestion. Consequently, cardiac work is decreased by virtue of the reduced cardiac output without affecting myocardial contractility, which contributes to improving cardiac function. Frank-Starling curve shown in FIG. 8A was parallel shifted right-downward with keeping the slope of the curve (representing myocardial contractility), and thereby indicating a reduction in preload.

(2) Influence of Afterload

Figure 8B:
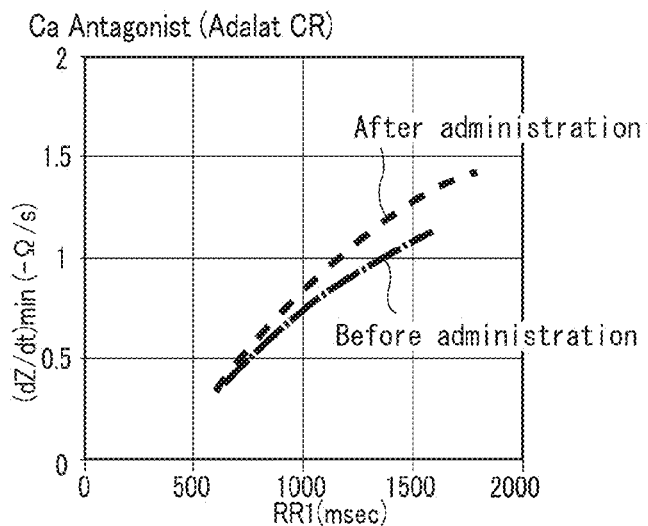
FIG. 8B shows administration of Ca antagonist (Adalat CR)

FIG. 8B shows a patient with hypertension and chronic atrial fibrillation treated with a calcium antagonist, Adalat CR (registered trademark) which is used as an antihypertensive drug. The dashed-dotted curve and the dotted curve represent before and after administration of Adalat CR respectively. The Frank-Starling curve before administration of Adalat CR (dashed-dotted curve) was shifted left-upward after the drug administration (dotted curve). This indicates that administration of Adalat CR dilates the peripheral arterial vessels, thereby resulting in a reduction in afterload and an increase in the blood volume ejected from the ventricle.

(3) Influence of Myocardial Contractility

Figure 8C:
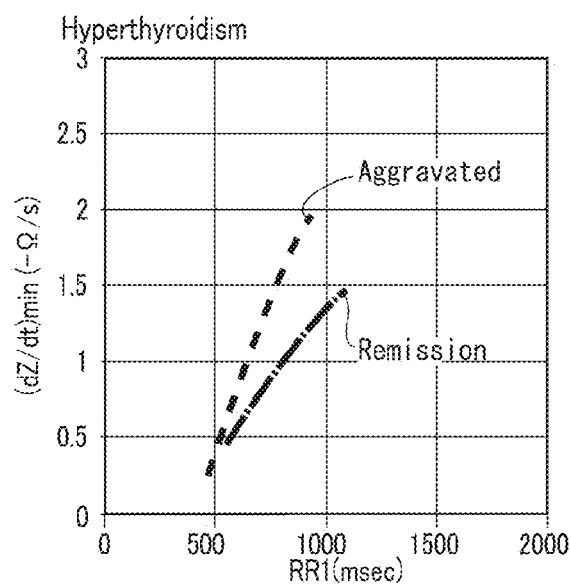
FIG. 8C shows hyperthyroidism, all of which affect the slope of the Frank-Starling curves.

FIG. 8C shows the above-described patient with hyperthyroidism and atrial fibrillation. The slope of the Frank-Starling curve during remission (dashed-dotted curve) was dramatically increased during aggravation (dotted curve). This indicates that the sympathetic activity is increased during aggravation of hyperthyroidism (because of enhanced β-adrenoreceptor activity caused by thyroid hormone excess), thereby resulting in an increase in myocardial contractility.

In this way, the Frank-Starling curve enables us to readily and visually evaluate the influence of three factors, namely preload, afterload, and myocardial contractility, on cardiac function in atrial fibrillation. Therefore, the method of the present invention for evaluating cardiac function provides very useful information for selecting effective drugs.

The method of the present invention may be useful for screening of new drugs because of being capable of distinguishing among three factors on cardiac function as described above.

Embodiment 4

Method for Simultaneously Displaying FSM and PESP on a Two-Dimensional Graph

Thoracic impedance measurement values of a total of 500 consecutive heart beats were obtained from a patient with atrial fibrillation. A two-dimensional scatter plot was created by using dots associated with the (dZ/dt)min values corresponding to RR1 values greater than RR2 values (PESP) identifiably superimposed on dots associated with the (dZ/dt)min values corresponding to RR1 values less than or equal to RR2 values (FSM), and the (dZ/dt)min values of FSM and PESP were applied to the y-axis against the corresponding RR1 values on the x-axis. Each approximate curve (i.e., logarithmic regression curve) was calculated using measurement values from each group of PESP dots and FSM dots.

An example is shown in FIG. 9. FIG. 9 shows a patient with mitral valve stenosis and chronic atrial fibrillation before (FIG. 9A) and after (FIG. 9B) administration of digitalis. The gray dots represent measurement values in the Frank-Starling mechanism (FSM), and the black dots represent measurement values in the postextrasystolic potentiation (PESP). The dotted line is the approximate curve of the group of FSM dots, and the solid line is the approximate curve of the group of PESP dots.

To date, digitalis has been mainly used to enhance parasympathetic activity, thereby resulting in relatively lower sympathetic activity, for decreasing heart rate in spite of unexpectedly weak inotropic action. When using this drug in patients with heart failure and atrial fibrillation, an increase in stroke volume is predicted by Frank-Starling mechanism associated with prolonged preceding RR intervals due to decrease in heart rate.

Decrease in heart rate with digitalis was verified by the center of dots representing the preceding RR interval (RR1) of about 1300 msec (heart rate 45/min) after administration of digitalis (FIG. 9B) in contrast to that representing the preceding RR interval (RR1) of about 800 msec (heart rate 74/min) before administration of the drug (FIG. 9A). The dotted FSM curve before administration of digitalis (FIG. 9A) was shifted right-upward with keeping the slope of the curve and the PESP curve was shifted right-downward with a decrease in the slope after administration of the drug (FIG. 9B). These results imply that the peak flow velocity of blood ejected from the ventricles, i.e., (dZ/dt)min, may be increased by Frank-Starling mechanism associated with prolonged preceding RR intervals due to decrease in heart rate with digitalis, while the sympathetic activity may be reduced, judging from PESP curve.

Thus, a single two-dimensional graph simultaneously displaying FSM and PESP makes it possible to evaluate the relationships among sympathetic activity, preload, afterload and myocardial contractility, which allows for a more detailed understanding of the pathophysiological mechanisms of cardiac function and providing useful information for the selection of therapeutic drugs and the observation of cardiac function.

Figure 10:
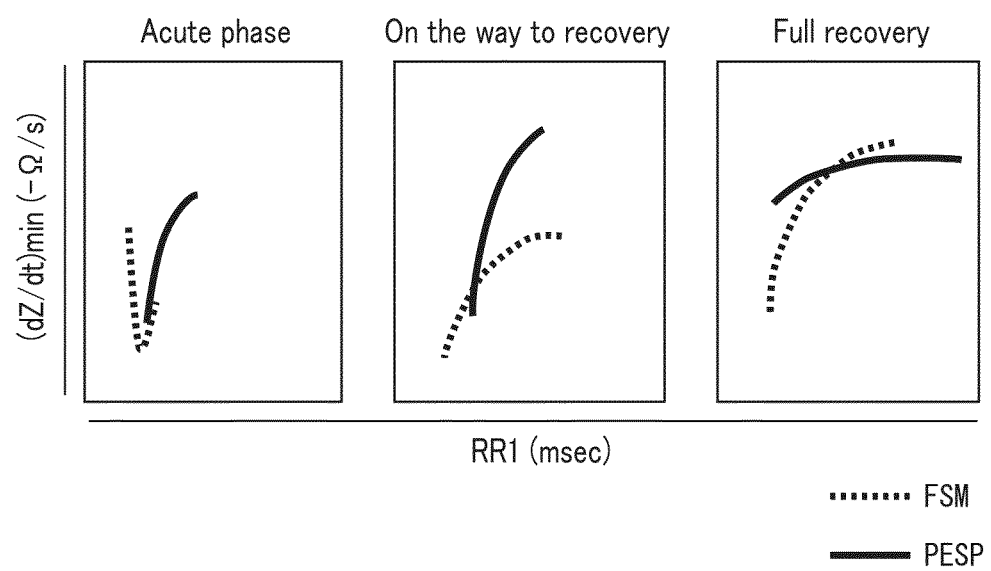
FIG. 10 schematically shows the recovery process of cardiac function exhibited by the relationship between the Frank-Starling curve and postextrasystolic potentiation curve.

FIG. 10 schematically shows the recovery process of cardiac function in patients with congestive heart failure and atrial fibrillation by using a single graph simultaneously displaying the two types of curves of the present invention, namely the Frank-Starling curve (dotted curve) and the PESP curve (solid curve). The present invention has revealed pathophysiological mechanisms of cardiac function during recovery from heart failure and has enabled clinicians to objectively perform a treatment, taking the mechanism of cardiac function into account by means of comparing the curve pattern of the present status of cardiac function in patients with heart failure with that of fully recovered patients.

Referred to the schematic diagram of FIG. 10, in the patient treated with digitalis shown in FIG. 9 as an embodiment, FIG. 9A indicates that the patient is on the way to recovery and FIG. 9B indicates that the patient is fully recovered.

Embodiment 5

Method for Displaying the Sum of (dZ/dt)min Values for FSM or PESP

A method for displaying the sum of the (dZ/dt)min values in FSM or PESP before and after treatment using an identifiable bar graph is described below. This method enables us to evaluate the degree of involvement of each mechanism in the recovery of cardiac function during treatment course and to use as an important indicator when considering selection of therapeutic drugs.

FIG. 11 shows a two-dimensional graph simultaneously displaying FSM and PESP, before and after treatment in the patient with exacerbation of heart failure and atrial fibrillation shown in FIG. 3. Referred to the schematic diagram of FIG. 10, FIG. 11A represents the acute phase of heart failure and FIG. 11B indicates that the patient is on the way to recovery, taking into account the relationship between the distribution pattern of dots in both FSM and PESP and each approximate curve. However, it is not enough to evaluate the degree of involvement of each mechanism of FSM and PESP in the recovery process of cardiac function.

Thoracic impedance measurement values of a total of 500 consecutive heart beats were obtained from a patient with atrial fibrillation. The sum of (dZ/dt)min values corresponding to RR1/RR2≤1 (FSM totals) and corresponding to RR1/RR2>1 (PESP totals) were calculated from the measurement values. These results were displayed on an identifiable bar graph as shown in FIG. 11C, by which the degree of involvement of FSM and PESP before and after treatment could be quantitatively exhibited.

In the present case, the involvement of PESP was apparently greater than that of FSM on improvement of cardiac function after treatment. This consequently suggests that by judging from improvement of subjective symptoms reported by patients, simplistic administering β-blocker, which is often used in the treatment of heart failure for suppression of sympathetic activity, may lead to result again in deterioration of cardiac function because of compromise of the contribution of PESP.

Evaluating the degree of involvement of the pathophysiological mechanisms in the recovery process of cardiac function, which can be obtained from each sum of (dZ/dt) min values in FSM and PESP, makes it possible to select appropriate therapeutic drugs and determine the time of administration of the drugs based on objective data in addition to subjective symptoms reported by patients, while considering only changes in the relationship between the distribution pattern of dots and approximate curve is not enough for therapeutic strategy.

Embodiment 6

Method for Simultaneously Displaying FSM and PESP on a Three-Dimensional Graph

In a single two-dimensional graph simultaneously displaying FSM and PESP, cardiac function cannot be visually and fully evaluated due in part to overlapping dots in FSM and PESP on the plane graph. However, when using a single three-dimensional scatter plot simultaneously displaying those, cardiac function can be visually and entirely assessed by separating the overlapping dots in them.

(dZ/dt)min values, preceding RR interval (RR1) values, pre-preceding RR interval (RR2) values, and RR1/RR2 ratio values were calculated using thoracic impedance measurement values of a total of 500 consecutive heart beats obtained from a patient with atrial fibrillation. A three-dimensional scatter plot was created by using dots associated with (dZ/dt)min values corresponding to RR1/RR2>1 (PESP) identifiably superimposed on dots associated with (dZ/dt)min values corresponding to RR1/RR2≤1 (FSM) and the corresponding RR1 values were applied to the x-axis, the corresponding RR1/RR2 ratio values were applied to the y-axis, and the corresponding (dZ/dt)min values were applied to the z-axis.

This three-dimensional scatter plot can separately display the distribution of dots in FSM and PESP, thereby being able to precisely detect small changes in cardiac function and provide very useful information on cardiac function and response to treatment in patients with atrial fibrillation.

Figure 12:
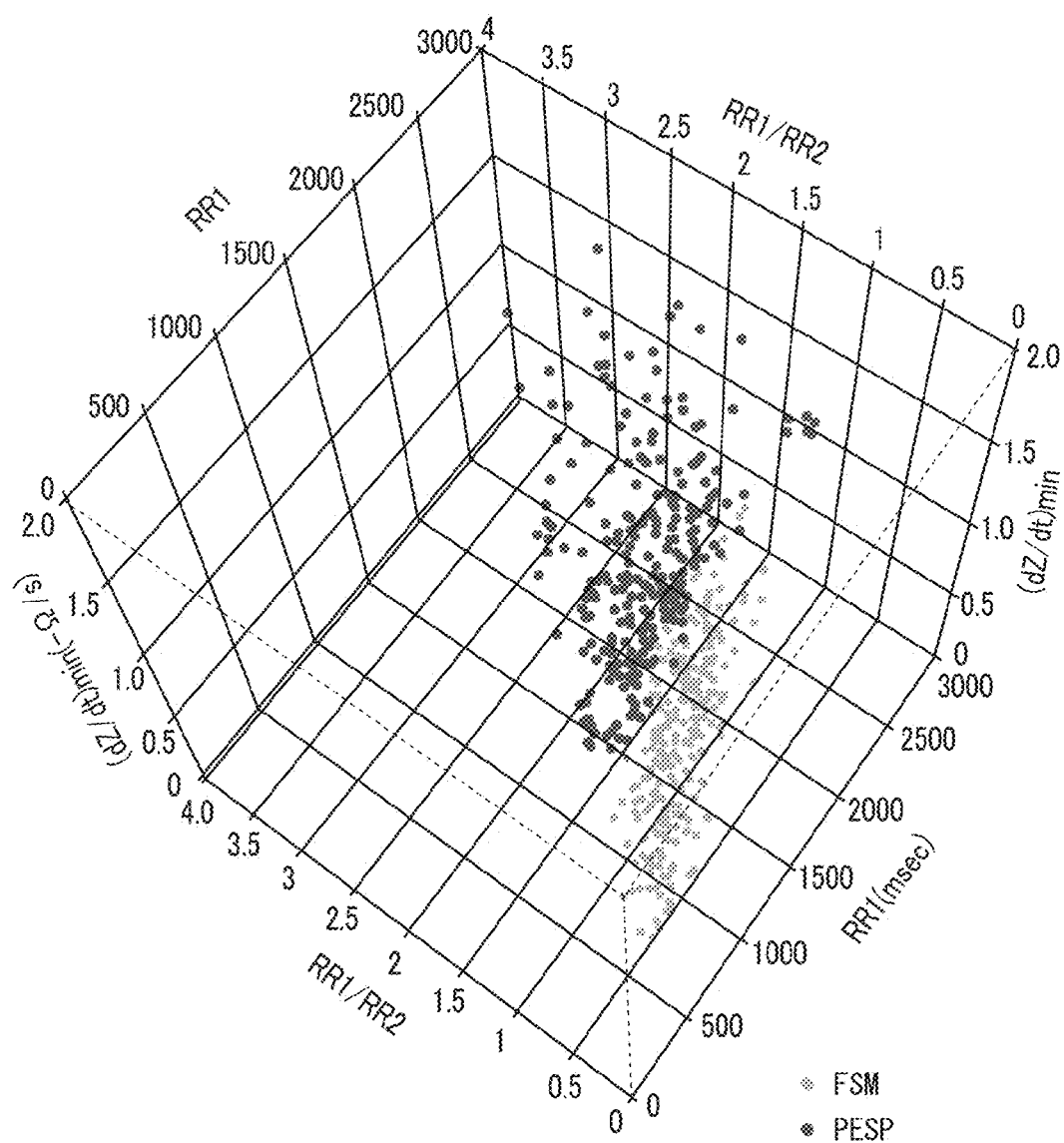
FIG. 12 shows a three-dimensional scatter plot representing the Frank-Starling mechanism and postextrasystolic potentiation.

FIG. 12 shows a single three-dimensional graph simultaneously displaying FSM and PESP in a patient with mitral valve stenosis and atrial fibrillation. The gray dots represent the Frank-Starling mechanism (FSM) and the black dots represent the postextrasystolic potentiation (PESP). In this graph, the distribution pattern of dots in FSM and PESP could be correctly evaluated by separating the overlapping dots of them, while dots in FSM and PESP were partially overlapped on the single two-dimensional graph. Thus, this method enables us to readily detect small differences in changes in the state of disease before and after administration of medication, and thereby being able to provide precise information on cardiac function to diagnose and treat the disease.

Embodiment 7

Application of the Method of the Present Invention to Heart Disease Other than Atrial Fibrillation FIG. 13 shows a pediatric patient with respiratory sinus arrhythmia. Respiratory sinus arrhythmia is a physiological phenomenon observed in children and is that heart rate is increased during inspiration and decreased during expiration. FIG. 13A shows a two-dimensional scatter plot simultaneously displaying the Frank-Starling mechanism (FSM) and the postextrasystolic potentiation (PESP). FIG. 13B shows the Frank-Starling curve, and FIG. 13C shows the PESP curve.

From these results, value of the slope of the approximate equation determined from the Frank-Starling curve in the healthy child was 2.6, which was characteristically greater than 2.0 compared to that in patients with atrial fibrillation. A value of the slope of that in patients with atrial fibrillation except for hyperthyroidism will be never greater than the 2.0 even if improving cardiac function. Thus, applying the 2.0 to a cut-off value of the slope of the Frank-Starling curve may allow for early detection of heart disease in children who cannot appropriately report subjective symptoms. Further, cardiac examination using the present method in preschool children has strong potential to early detect pediatric congenital heart disease.

The present method can be used as evaluation of cardiac function not only in children with respiratory sinus arrhythmia but also in athletes with sinus arrhythmia and bradycardia as well as in patients with sick sinus syndrome.

Embodiment 8

System Diagram of Control Block of the Evaluation System in Cardiac Function Based on Thoracic Impedance Measurements The analytical method of the present invention described in embodiments 1 to 7 can be executed in a computer program. The method of the present invention is built as a system with a thoracic impedance device.

Figure 14:
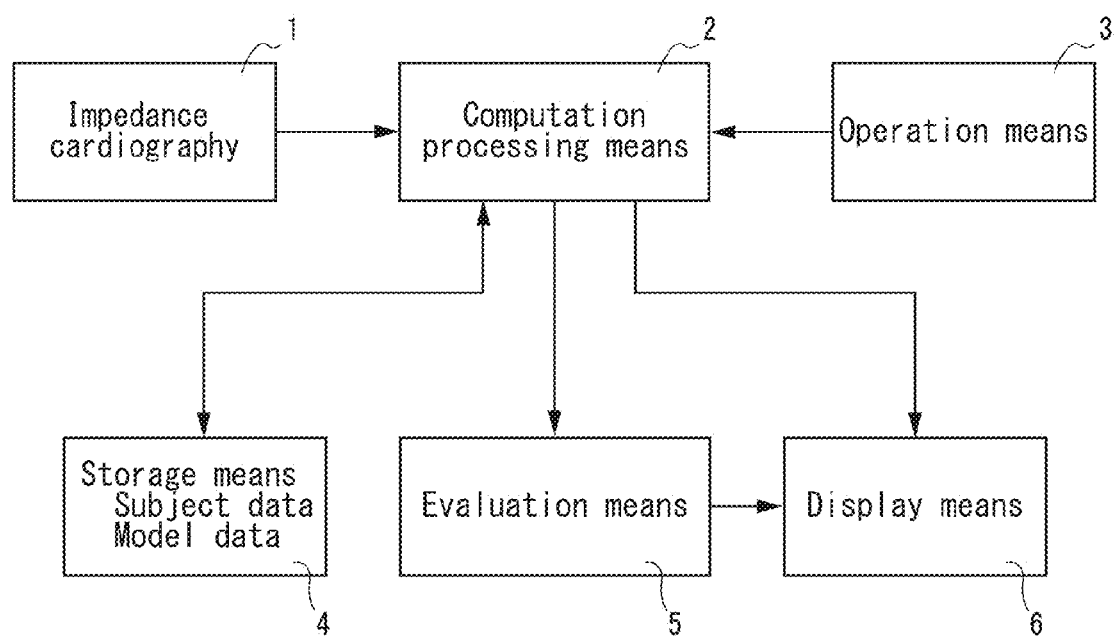
FIG. 14 shows a system diagram of control block of evaluation system in cardiac function based on thoracic impedance measurements according to the embodiments of the present invention.

FIG. 14 shows an evaluation system in cardiac function using the present invention. An impedance cardiography 1 for measuring thoracic impedance is connected to computation processing means 2, which is comprised of a computer and the like for evaluating cardiac function using data obtained by the impedance cardiography 1.

Furthermore, the computation processing means 2 is connected to both operation means 3 for carrying out computation processing operations and storage means 4 for storage and saving of data which are computationally processed by the computation processing means 2. Thoracic impedance data obtained by measurements of different periods in a same patient, model data in patients with various heart disease, and data in healthy subjects are stored in the storage means 4. Although not described in the figure above, thoracic impedance data, graphs and model data obtained by measurements of different periods in a same patient can be picked out by a picking mechanism. Display means 6 capable of identifiably displaying superimposed approximate curves, and the like of different periods is also provided. Data compared with model data by evaluation means 5 assessing changes in the disease can be displayed in various forms of graphs and approximate curves by the display means 6.

Since cardiac function can be visually evaluated by the display means 6, it is possible to provide the information necessary for diagnosis in an easy manner for clinicians.

The system of the present invention is composed of a very small, simple mobile device, and can be easily operated by everybody other than a clinician. The system can also be used as a cardiac function test for patients receiving home medical care and for those living in areas with insufficient medical care. When using Internet, the data of patients obtained by a visiting care team or a mobile care team will be transferred to a hospital staffed with clinicians who can provide, from a distance, a strategy for diagnosis and treatment.

Using the present invention in this manner makes it possible to evaluate cardiac function in a patient on the basis of objective data obtained by means of comparing the distribution pattern of dots in the patient with that in patients associated with typical disease conditions stored in the storage unit.

The invention claimed is:

1. A method for diagnosing cardiac function in a patient with atrial fibrillation, comprising:
    measuring continuous thoracic impedance values from the patient with atrial fibrillation using cardiac function measurement means;
    obtaining, using a processor, (dZ/dt)min values, and corresponding preceding RR interval (RR1) values, pre-preceding RR interval (RR2) values and RR1/RR2 ratio values, by processing the continuous thoracic impedance values measured using the cardiac function measurement means;
    displaying, on a display controlled by said processor, the (dZ/dt)min values, and the corresponding preceding RR interval (RR1) values, pre-preceding RR interval (RR2) values and RR1/RR2 ratio values, in a scatter plot in which RR1 or RR1/RR2 is used for one axis and (dZ/dt)min is used for another axis; and
    diagnosing cardiac function in the patient with atrial fibrillation by comparing the scatter plot displaying (dZ/dt)min values, and the corresponding preceding RR interval (RR1) values, pre-preceding RR interval (RR2) values and RR1/RR2 ratio values, with predefined model data.

2. The method for diagnosing cardiac function according to claim 1, wherein
    the obtained (dZ/dt)min values corresponding to RR1 values are displayed, on the display controlled by said processor, in a two-dimensional scatter plot, where RR1 is used for the X-axis and (dZ/dt)min is used for the Y-axis; and
    the two-dimensional scatter plot displaying RR1 and (dZ/dt)min is compared with predefined model data to diagnose cardiac function in the patient with atrial fibrillation.

3. The method for diagnosing cardiac function according to claim 2, comprising:
    determining an approximated curve from the data of the scatter plot; and
    displaying measurement values with the approximated curve superimposed on the scatter plot; and
    diagnosing cardiac function in the patient with atrial fibrillation based on the scatter plot and the approximated curve superimposed on the scatter plot.

4. The method for diagnosing cardiac function according to claim 1, wherein displaying (dZ/dt)min values, and the corresponding preceding RR interval (RR1) values, pre-preceding RR interval (RR2) values and RR1/RR2 ratio values on the scatter plot in which RR1 or RR1/RR2 is used for one axis and (dZ/dt)min is used for another axis includes:
    selecting, using the processor, (dZ/dt)min values when RR1 value corresponding to (dZ/dt)min value is greater than corresponding RR2 value; and
    displaying, on the display controlled by said processor, the selected (dZ/dt)min values and the corresponding RR1/RR2 ratio values as a two-dimensional scatter plot in which RR1/RR2 is used for the X-axis and the (dZ/dt)min is used for the Y-axis,
    wherein the resulting two-dimensional scatter plot is demonstrated as a two-dimensional scatter plot for displaying (dZ/dt)min values representing postextrasystolic potentiation (PESP), and
    wherein the resulting two-dimensional scatter plot is compared with predefined model data to diagnose cardiac function in the patient with atrial fibrillation.

5. The method for diagnosing cardiac function according to claim 4, comprising:
    determining an approximated curve from the data of the scatter plot; and
    displaying measurement values with the approximated curve superimposed on the scatter plot; and
    diagnosing cardiac function in the patient with atrial fibrillation based on the scatter plot and the approximated curve superimposed on the scatter plot.

6. The method for diagnosing cardiac function according to claim 1, wherein displaying (dZ/dt)min values, and corresponding preceding RR interval (RR1) values, pre-preceding RR interval (RR2) values and RR1/RR2 ratio values on the scatter plot in which RR1 or RR1/RR2 is used for one axis and (dZ/dt)min is used for another axis includes:
    selecting, using the processor, (dZ/dt)min values when RR1 corresponding to (dZ/dt)min value is equal to or less than corresponding RR2 value; and
    displaying, on the display controlled by said processor, the selected (dZ/dt)min values and the corresponding RR1 values as a two-dimensional scatter plot in which RR1 is used as the X-axis and the (dZ/dt)min is used as the Y-axis,
    wherein the resulting two-dimensional scatter plot is demonstrated as a two-dimensional scatter plot for displaying the (dZ/dt)min values representing the Frank-Starling Mechanism that do not involve postextrasystolic potentiation, and
    wherein the resulting two-dimensional scatter plot is compared with predefined model data to diagnose cardiac function in the patient with atrial fibrillation.

7. The method for diagnosing cardiac function according to claim 6, comprising:

determining an approximated curve from the data of the scatter plot; and displaying measurement values with the approximated curve superimposed on the scatter plot; and diagnosing cardiac function in the patient with atrial fibrillation based on the scatter plot and the approximated curve superimposed on the scatter plot.

8. The method for diagnosing cardiac function according to claim 1, wherein displaying (dZ/dt)min values, and corresponding preceding RR interval (RR1) values, pre-preceding RR interval (RR2) values and RR1/RR2 ratio values on the scatter plot in which RR1 or RR1/RR2 is used for one axis and (dZ/dt)min is used for another axis includes:

selecting, using the processor, (dZ/dt)min values (dZ/dt)min values representing postextrasystolic potentiation when RR1 value corresponding to (dZ/dt)min value is greater than corresponding RR2 value;

selecting, using the processor, (dZ/dt)min values as (dZ/dt)min values representing Frank-Starling Mechanism that do not involve postextrasystolic potentiation when RR1 value corresponding to (dZ/dt)min value is equal to or less than corresponding RR2 value;

displaying, on the display controlled by said processor, so as to be identifiably superimposed as two sets of data in a two-dimensional scatter plot in which RR1 is used as the X-axis and (dZ/dt)min is used as the Y-axis, a set of the selected (dZ/dt)min values representing postextrasystolic potentiation and the corresponding RR1 values, and another set of the selected (dZ/dt)min values representing the Frank-Starling Mechanism that do not involve postextrasystolic potentiation and the corresponding RR1 values, wherein the resulting two-dimensional scatter plot is compared with predefined model data to diagnose cardiac function in the patient with atrial fibrillation.

9. The method for diagnosing cardiac function according to claim 8, comprising:

determining an approximated curve from the data of the scatter plot;

displaying measurement values with the approximated curve superimposed on the scatter plot; and diagnosing cardiac function in the patient with atrial fibrillation based on the scatter plot and the approximated curve superimposed on the scatter plot.

10. The method for diagnosing cardiac function according to claim 1, wherein displaying (dZ/dt)min values, and corresponding preceding RR interval (RR1) values, pre-preceding RR interval (RR2) values and RR1/RR2 ratio values on the scatter plot in which RR1 or RR1/RR2 is used for one axis and (dZ/dt)min is used for another axis includes:

selecting, using the processor, (dZ/dt)min values as (dZ/dt)min values representing postextrasystolic potentiation when RR1 value corresponding to (dZ/dt)min value is greater than corresponding RR2 value;

selecting, using the processor, (dZ/dt)min values as (dZ/dt)min values representing Frank-Starling Mechanism that do not involve postextrasystolic potentiation when RR1 value corresponding to (dZ/dt)min value is the same as or less than corresponding RR2;

displaying, on the display controlled by said processor, so as to be identifiably superimposed as two sets of data in a three-dimensional scatter plot in which RR1 is used as the X-axis, RR1/RR2 is used as the Y-axis, and (dZ/dt)min is used as the Z-axis, a set of the selected (dZ/dt)min values representing postextrasystolic potentiation and the corresponding RR1 values and RR1/RR2 ratio values, and another set of the selected (dZ/dt)min values representing the Frank-Starling Mechanism that do not involve postextrasystolic potentiation and the corresponding RR1 values and RR1/RR2 ratio values, and wherein the resulting three-dimensional scatter plot is compared with predefined model data to diagnose cardiac function.

11. The method for diagnosing cardiac function according to claim 10, comprising:

determining an approximated curve from the data of the scatter plot; and displaying measurement values with the approximated curve superimposed on the scatter plot; and diagnosing cardiac function in the patient with atrial fibrillation based on the scatter plot and the approximated curve superimposed on the scatter plot.

12. A method for diagnosing cardiac function in a patient with atrial fibrillation, comprising:

measuring, using cardiac function measurement means, thoracic impedance measurement values at different time points in a same patient with atrial fibrillation;

obtaining, using a processor, (dZ/dt)min values, and corresponding preceding RR interval (RR1) values, pre-preceding RR interval (RR2) values and RR1/RR2 ratio values, by processing the thoracic impedance values measured using the cardiac function measurement means;

displaying, on a display controlled by said processor, the (dZ/dt)min values, and the corresponding preceding RR interval (RR1) values, pre-preceding RR interval (RR2) values and RR1/RR2 ratio values obtained from the thoracic impedance measurement values measured at different time points so as to be identifiably superimposed by each time point in a scatter plot in which RR1 or RR1/RR2 is used for one axis and (dZ/dt)min is used for another axis; and diagnosing cardiac function in the patient with atrial fibrillation by comparing the superimposedly displayed pattern at different time points in the scatter plot with data patterns of pre-stored model data.

13. The method for evaluating cardiac function according to claim 12, comprising:

determining an approximated curve from data of the scatter plot; and displaying the approximated curve superimposed on the scatter plot, and diagnosing cardiac function based on the scatter plot and the approximated curve superimposed on the scatter plot.

14. The method for diagnosing cardiac function according to claim 1, further comprising:

determining an approximated curve from data of the scatter plot; and displaying the approximated curve superimposed on the scatter plot.

* * * * *